United States Patent [19]

Harris

[11] Patent Number: 4,866,198

[45] Date of Patent: * Sep. 12, 1989

[54] CALIXARENE DERIVATIVES AND USE AS ACCELERATORS IN ADHESIVE COMPOSITIONS

[75] Inventor: Stephen J. Harris, Dublin, Ireland

[73] Assignee: Loctite Corporation, Newington, Conn.

[*] Notice: The portion of the term of this patent subsequent to Dec. 3, 2002 has been disclaimed.

[21] Appl. No.: 88,945

[22] Filed: Aug. 24, 1987

Related U.S. Application Data

[60] Continuation-in-part of Ser. No. 914,491, Oct. 2, 1986, Pat. No. 4,718,966, which is a division of Ser. No. 776,536, Sep. 16, 1985, Pat. No. 4,556,700, which is a continuation-in-part of Ser. No. 575,257, Jan. 30, 1984, abandoned, and a continuation-in-part of Ser. No. 825,012, Jan. 31, 1986, Pat. No. 4,695,615, which is a continuation-in-part of Ser. No. 717,251, Mar. 28, 1985, Pat. No. 4,642,362, and a continuation-in-part of Ser. No. 870,677, Jun. 4, 1986, Pat. No. 4,699,966, which is a continuation-in-part of Ser. No. 717,251, Mar. 28, 1985, Pat. No. 4,642,362.

[30] Foreign Application Priority Data

Aug. 29, 1986 [IE] Ireland ............................ 2318/86

[51] Int. Cl.$^4$ ............................................ C07C 69/76
[52] U.S. Cl. .................................. 560/61; 560/62; 568/325
[58] Field of Search ................. 560/55, 60, 61, 62; 568/325

[56] References Cited

U.S. PATENT DOCUMENTS

| | | | |
|---|---|---|---|
| 4,171,416 | 10/1979 | Motegi et al. | 526/245 |
| 4,386,193 | 5/1983 | Reich et al. | 526/298 |
| 4,477,377 | 10/1984 | Izatt et al. | |
| 4,556,700 | 12/1985 | Harris | 526/209 |
| 4,617,336 | 10/1986 | Pastor | 524/291 |
| 4,622,414 | 11/1986 | McKervey | 560/61 |
| 4,636,539 | 1/1987 | Harris et al. | 523/214 |
| 4,642,362 | 2/1987 | Harris et al. | 556/419 |
| 4,695,615 | 9/1987 | Leonard et al. | 526/194 |
| 4,699,966 | 10/1987 | Harris et al. | 528/12 |

OTHER PUBLICATIONS

J. Chem. Soc., Comm., 981–982 (1984).
J. Inclusion Phenomena, 2, 199–206 (1984).
Chem. Letters, pp. 477–478 (1984).
Acc. Chem. Res., 1983, 16, 161–170 ("Gutsche").

Primary Examiner—Christopher Henderson
Attorney, Agent, or Firm—Vidas & Arrett

[57] ABSTRACT

Novel Calixarene derivatives useful as accelerators in cyanoacrylate adhesive compositions are represented by the formula

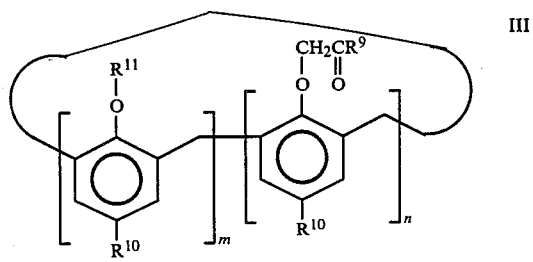

wherein
m+n=4,6 or 8
n=an integer greater than or equal to $\frac{1}{2}$ (m+n)
$R^9$ is aryl, hydrocarbylaryl, aryloxy, hydrocarbylaryloxy, substituted aryl, substituted hydrocarbylaryl, substituted aryloxy or substituted hydrocarbylaryloxy; or when $R^{10}$ is aryl, hydrocarbylaryl, substituted aryl or substituted hydrocarbylaryl, $R^9$ is hydrocarbyl, hydrocarbyloxy, substituted hydrocarbyl or substituted hydrocarbyloxy;
$R^{10}$ is H, hydrocarbyl, aryl, hydrocarbylaryl, substituted hydrocarbyl, substituted aryl or substituted hydrocarbylaryl;
$R^{11}$ is H, hydrocarbyl or substituted hydrocarbyl;
provided that neither $R^9$ or $R^{11}$ is substituted with a basic N-containing group.

9 Claims, No Drawings

CALIXARENE DERIVATIVES AND USE AS ACCELERATORS IN ADHESIVE COMPOSITIONS

This application is a continuation-in-part of Ser. No. 914,491, filed Oct. 2, 1986, now U.S. Pat. No. 4,718,966, which is a division of Ser. No. 776,536, filed Sept. 16, 1985, now U.S. Pat. No. 4,636,539, which is a division of Ser. No. 673,621, filed Nov. 21, 1984, now U.S. Pat. No. 4,556,700, which is a continuation-in-part of Ser. No. 575,257, filed Jan. 30, 1984, now abandoned. This application is also a continuation-in-part of Ser. No. 825,012 filed Jan. 31, 1986, now U.S. Pat. No. 4,695,615, which is a continuation-in-part of Ser. No. 717,251, filed Mar. 28, 1985, now U.S. Pat. No. 4,642,362. This application is also a continuation in part of Ser. No. 870,677, filed June 4, 1986, now U.S. Pat. No. 4,699,966, which is a continuation-in-part of Ser. No. 717,251, filed Mar. 28, 1985, now U.S. Pat. No. 4,642,362.

BACKGROUND OF THE INVENTION (a) Field of the Invention

This invention relates to novel calixarene derivatives and to cyanoacrylate adhesive compositions which contain such calixarene derivatives as accelerators.

(b) Description of Related Art

U.S. Pat. No. 4,556,700 Harris et al describes the use in cyanoacrylate adhesive compositions of calixarene compounds represented by the formula

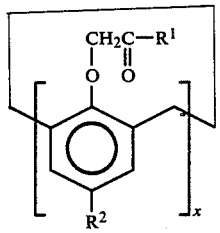

where $R^1$ is alkyl, alkoxy, substituted alkyl or substituted alkoxy, $R^2$ is H or alkyl and $x=4$, 6 or 8.

European Patent Application No. 0196895 A2 describes the use in cyanoacrylate adhesive compositions of calixarene compounds represented by the formula

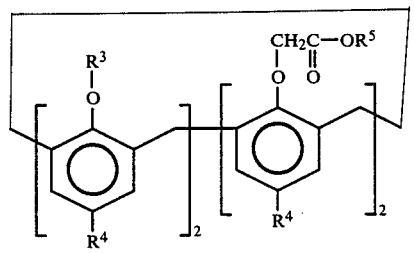

where $R^3$ is H, $-CH_2COOH$, $-CH_2COOR^6$, $-COR^8$, hydrocarbyl or trihydrocarbylsilyl or the two $R^3$ groups together form a divalent hydrocarbyl or oxygen interrupted hydrocarbyl group; $R^4$ is H or hydrocarbyl; $R^5$ is hydrocarbyl, hydrocarbyl interrupted by one or more oxygen atoms or hydrocarbyl substituted with halo, oxo or nitro groups;

$R^6$ is as defined for $R^5$ but is a different group therefrom; and $R^8$ is as defined for $R^5$ but may be the same or different therefrom.

SUMMARY OF THE INVENTION

Another class of calixarene compounds which has now been discovered to be highly useful in cyanoacrylate adhesive compositions are novel calixarene derivatives represented by the formula

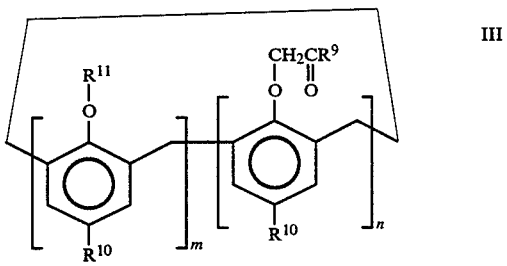

wherein
$m+n=4$, 6 or 8
$n=$an integer greater than or equal to $\frac{1}{2}$ (m+n)
$R^9$ is aryl, hydrocarbylaryl, aryloxy, hydrocarbylaryloxy, substituted aryl, substituted hydrocarbylaryl, substituted aryloxy or substituted hydrocarbylaryloxy; or when $R^{10}$ is aryl, hydrocarbylaryl, substituted aryl or substituted hydrocarbylaryl, $R^9$ is hydrocarbyl, hydrocarbyloxy, substituted hydrocarbyl or substituted hydrocarbyloxy;

$R^{10}$ is H, hydrocarbyl, aryl, hydrocarbylaryl, substituted hydrocarbyl, substituted aryl or substituted hydrocarbylaryl; $R^{11}$ is H, hydrocarbyl or substituted hydrocarbyl; provided that neither $R^9$ or $R^{11}$ is substituted with a basic N-containing group.

When m and n are greater than 1, the m aryl groups having the $-OR^{11}$ side chain may be interspersed around the ring between the n aryl groups having the $-OCH_2C(O)R^9$ side chain.

In the above formula, hydrocarbyl is suitably alkyl or alkenyl; alkyl or alkenyl preferably has 1–10 carbon atoms, more particularly 1–5 carbon atoms. If $R^9$, $R^{10}$ or $R^{11}$ is substituted, it may suitably be substituted with one or more halo or oxo groups.

The present invention provides new cyanoacrylate compositions for bonding wood and other de-activating surfaces such as paper, leather, ceramics, plastics and metals with chromate treated or acidic oxide surfaces. The inventive compositions are stranded cyanoacrylate adhesive formulations to which have been added, as accelerators, calixarene compounds as defined above which are stable to cyanoacrylate monomers. The calixarene compounds are employed in amounts conventional for cyanoacrylate accelerators, preferably at levels betwee about 0.1% and 2% by weight of the composition.

The standard alpha-cyanoacrylate compositions are as described as U.S. Pat. No. 4,556,700 Harris et al at column 2 line 18—column 3 line 32, the contents of which are incorporated herein by reference.

Calixarene compounds may be readily synthesised by methods described in C. Gutsche, Acc. Chem. Res., 16, 161-170 (1983) and references cited therein; U.S. Pat. No. 4,556,700 Harris et al; and in Journal of Inclusion Phenomena 2 199–206 (1984) D Reidel Publishing Company; the appropriate dsclosures of all of which are incorporated herein by reference.

DESCRIPTION OF THE PREFERRED EMBODIMENTS

The invention may be further understood with reference to the following non-limiting examples.

EXAMPLE 1

Preparation of

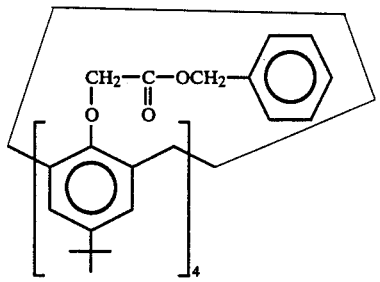
IV

To 2.48 g of the tetraethylacetate of p-t-butylcalix-4-arene (0.0025 mole) (prepared as in Example 8 of U.S. Pat. No. 4,556,700 Harris et al) was added 5.4 g (0.050 mole) benzyl alcohol and 40 mg p-toluene sulphonic acid transesterification catalyst and the entire was stirred under nitrogen at 120°-130° for 48 hours. The reaction mixture was then allowed to cool and the excess benzyl alcohol distilled off under vacuum to give 3.0 g of a clear buff colored solid which was taken up in dichloromethane, washed well twice with water, then dried over magnesium sulphate to give after removal of volatiles 2.9 g off-white solid m.pt. 67°-8° C. characterised by i.r. spectroscopy and elemental analysis as the compound of formula IV above i.r. Spectroscopy results: $\nu 1750(S) cm^{-1} C=O$ Elemental Analysis results=(Calc'd for $C_{80}H_{88}O_{12}$, C: 77.39, H: B 7.14, O: 15.47; Found, C: 77.38, H: 7.43, O: 15.08)

Preparation of Tetramer Starting Materials A & B

Preparation of

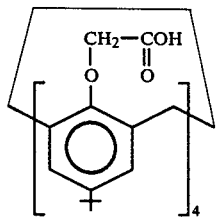
A 34.0 g tetraethylacetate of p-t-butyl calix-4-arene (0.034 mole) (prepared as in U.S. Pat. No. 4,556,700 Harris et al) was refluxed for 72 hours with 76.0 g KOH (1.35 mole), 70 mls IMS and 70 mls water. The reaction mixture was then added to 200 mls 35% aqueous HCl and the white solid was filtered and washed several times with water to remove acid and then dried to give 26.0 g of product characterised by i.r. spectroscopy as the acid derivative of formula A above.

Preparation of

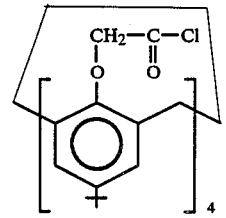
B

To 4.4 g (0.005 mole) of the acid derivative of formula A prepared above in 91 mls dry dichloromethane was added 21.6 g oxalyl chloride with stirring under nitrogen at room temperature dropwise during 30 minutes. After several hours the white suspension had completely dissolved giving a clear pale yellow liquid which was left stirring at room temperature overnight. After removal of volatiles 4.77 g colourless solid was left identified by i.r. spectroscopy as the acid chloride of formula B above which was not further purified in view of its moisture sensitivity.

EXAMPLE 2

Preparation of

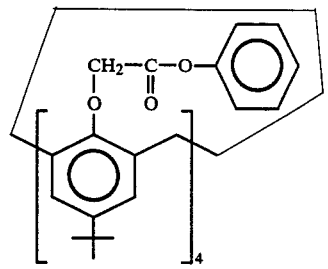
V

To 3.08 g (0.0032 mole) of the acid chloride starting material of formula B in 20 mls NaH dried THF (tetrahydrofuran) at 0° C. was added dropwise 2.04 g (0.026 mole) dry pyridine and 2.45 g (0.026 mole) phenol under nitrogen with stirring during 15 minutes. A white precipitate formed and the stirred reaction mixture was allowed to warm to room temperature and left stirring 72 hours. The reaction mixture was then poured into 100 mls ice water and then extracted with dichloromethane which was washed well twice with water and then dried over magnesium sulphate to give after removal of volatiles 3.0 g crude white solid product. Recrystallisation from IMS gave 2.6 g colourless crystalline product m.pt. 154°-5° C. characterised by i.r. spectroscopy and elemental analysis as the compound of formula V above.

i.r. Spectroscopy results: $\nu 1765(s) cm^{-1}$ C=O, $1583(m) cm^{-1} C \ldots C$ Elemental Analysis results=(Calc'd for $C_{76}H_{80}O_{12}$, C: 77.00, H: 6.80, O: 16.20; Found, C: 76.44, H: 7.00, O:15.75)

EXAMPLE 3

Preparation of

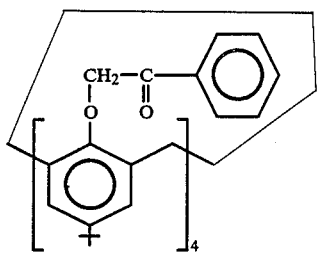

VI

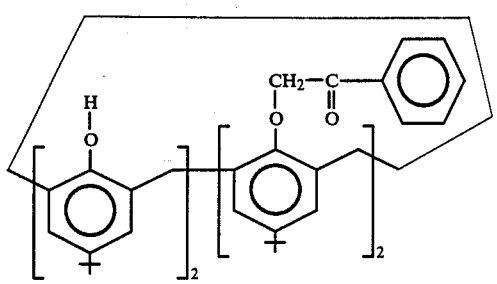

VII

A mixture of 9.72 g (0.015 mole) p-t-butylcalix-4-arene 18.6 g (0.120 mole) phenacyl chloride, 9.96 (0.060 mole) anhydrous potassium iodide, 12.42 g (0.090 mole) anhydrous potassium carbonate and 600 mls analar acetone was refluxed under dry nitrogen with stirring for 68 hours. After this time the cooled reaction mixture was poured into 1 liter ice water and the orange-coloured solid filtered off, washed with 5% aqueous hydrochloric acid, followed by water then dried over $P_2O_5$ in a dessicator to give 12.1 g crude orange solid product. This product was chromatographed on neutral alumina using 50:50 dichloromethane, 40°-60° C. petroleum ether as eluent to give after removal of solvent off-white solid product m.pt. 141°-8° characterised by i.r. spectroscopy, HPLC (High pressure liquid chromatography) and elemental analysis as the compound of formula VI above mixed with 20% dietherified product of formula VII above.

i.r. spectroscopy results: $\nu1680(s)cm^{-}C\!=\!O$

HPLC Analysis results=Employing Waters Associates Model 440 and micro Bondapak C18 reverse phase column. U.V. detector Pye unicam PU4020 set at $\lambda$m 280 nm 1.5 mls/minute (10% water, 90% THF) (Isocratic)=3.13 minutes elution volume—main product of formula VI, 2.27 minutes elution volume—20% secondary product of formula VII Elemental analysis results=(Calc'd for $C_{76}H_{80}O_8$, C: 81.39, H: 7.19, O: 11.41; Found C: 82.21, H: LB 6.59, O: 10.72) [Calc'd for the compound of formula VII, $C_{60}H_{68}O_6C$: 81.41, H: 7.74, O: 10.85]

EXAMPLE 4

Preparation of

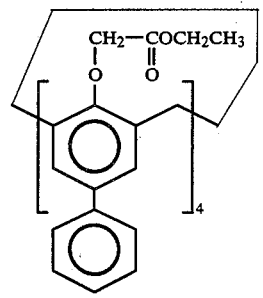

VIII

To 0.566 g (0.00078 mole) p-phenylcalix-4-arene (obtained from Parish Chemicals USA) was added 1.04 g (0.0062 mole) ethyl bromoacetate and 0.64 g (0.0047 mole) anhydrous potassium carbonate and 5 mls dry analar acetone and the mixture was refluxed together under nitrogen for 7 days after which the cooled reaction mixture was poured into 50 mls 5% aqueous HCl and an off-white coloured solid precipitated. This solid was filtered off and washed with water to give 0.83 g crude product which after air-drying was chromatographed on neutral alumina using dichloromethane as eluent. After removal of solvent a colourless solid was obtained m.pt. 53°-4° C. characterised by i.r. spectroscopy and elemental analysis as the compound of formula VIII above.

I.R. spectroscopy results: $\nu1745(s)cm^{-1}$ C=O

Elemental analysis results=(Calc'd for $C_{68}H_{64}O_{12}$, C: 76.10, H: 6.00, Found, C: 75.66, H: 6.16)

EXAMPLE 5

Ethyl cyanoacrylate stabilised with 10 parts per million $BF_3$ was used as a base adhesive formulation. The calixarene compounds listed in table I below were dissolved in the base adhesive at the indicated levels, and fixture times on copy paper and on white deal were determined.

The results shown below demonstrate the very good accelerative activity for these Calixarenes:

TABLE I

| Additive | Amount | Fixture Time Copy Paper | White Deal |
|---|---|---|---|
| None | — | 60 seconds | 5-6 minutes |
| Example 1 | 0.5% | 1-3 seconds | 20-25 seconds |
| Example 2 | 0.5% | 1-3 seconds | 30-40 seconds |
| Example 3 | 0.5% | 1-3 seconds | 10-15 seconds |
| Example 4 | 0.5% | 20 seconds | 30-40 seconds |
| Tetraethylacetate of p-t-butylcalix-4-arene (see Example 8 of U.S. Pat. No. 4 556 700) | 0.5% | 1 second | 30-40 seconds |

I claim:

1. Novel calixarene derivatives represented by the formula:

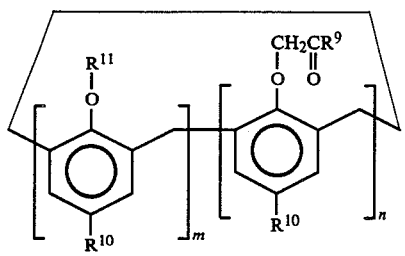

wherein:

m+n=4, 6 or 8;

n=an integer greater than or equal to ½(m+n);

$R^9$ is aryl, hydrocarbylaryl, aryloxy, hydrocarbylaryloxy, substituted aryl, substituted hydrocarbylaryl, substituted aryloxy or substituted hydrocarbylaryloxy; or when $R^{10}$ is aryl, hydrocarbylaryl, substituted aryl or substituted hydrocarbylaryl, $R^9$ is hydrocarbyl, hydrocarbyloxy, substituted hydrocarbyl or substituted hydrocarbyloxy;

$R^{10}$ is H, hydrocarbyl, aryl, hydrocarbylaryl, substituted hydrocarbyl, substituted aryl or substituted hydrocarbylaryl; $R^{11}$ is H, hydrocarbyl or substituted hydrocarbyl;

and the said substitutions on the $R^9$, $R^{10}$ and $R^{11}$ groups are selected from the group consisting of halo or oxo groups.

2. Calixarene derivatives according to claim 1 wherein hydrocarbyl is alkyl or alkenyl having 1–10 carbon atoms.

3. Calixarene derivatives according to claim 2 wherein hydrocarbyl is alkyl or alkenyl having 1–5 carbon atoms.

4. Calixarene derivatives according to claim 1 wherein m=0, n=4, $R^9$ is aryl, aryloxy or alkaryloxy and $R^{10}$ is alkyl.

5. Calixarene derivatives according to claim 1 wherein m=0, n=4, $R^9$ is alkoxy and $R^{10}$ is aryl.

6. Calixarene derivative according to claim 1 of the formula

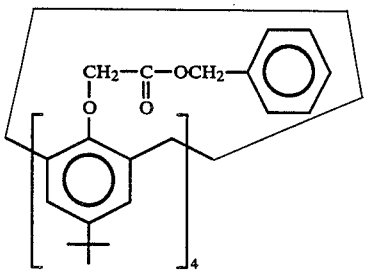

7. Calixarene derivative according to claim 1 of the formula

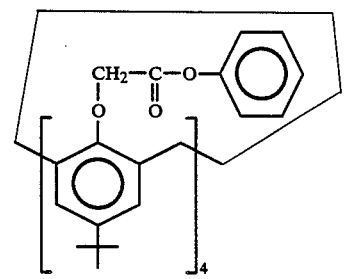

8. Calixarene derivative according to claim 1 of the formula

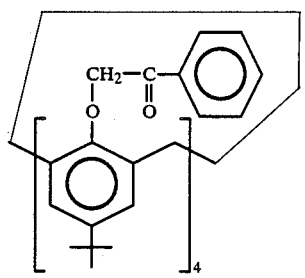

9. Calixarene derivative according to claim 1 of the formula

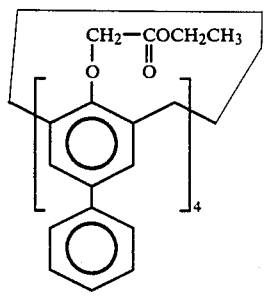

* * * * *